(12) United States Patent
McLintock (10) Patent No.: US 10,365,223 B2
(45) Date of Patent: Jul. 30, 2019

(54) ANALYTICAL METHOD USING SURFACE ENHANCED RAMAN SPECTROSCOPY AND COMPOSITION FOR THE METHOD

(71) Applicant: JOHNSON MATTHEY PUBLIC LIMITED COMPANY, London (GB)

(72) Inventor: Alison McLintock, Billingham (GB)

(73) Assignee: Johnson Matthey Public Limited Company, London, England (GB)

( * ) Notice: Subject to any disclaimer, the term of this patent is extended or adjusted under 35 U.S.C. 154(b) by 107 days.

(21) Appl. No.: 15/517,079

(22) PCT Filed: Oct. 16, 2015

(86) PCT No.: PCT/GB2015/053087
§ 371 (c)(1),
(2) Date: Apr. 5, 2017

(87) PCT Pub. No.: WO2016/059429
PCT Pub. Date: Apr. 21, 2016

(65) Prior Publication Data
US 2017/0307531 A1 Oct. 26, 2017

(30) Foreign Application Priority Data
Oct. 17, 2014 (GB) .................................. 1418483.2

(51) Int. Cl.
*G01N 21/65* (2006.01)
*B82Y 30/00* (2011.01)
*G01N 21/27* (2006.01)

(52) U.S. Cl.
CPC ............ *G01N 21/658* (2013.01); *B82Y 30/00* (2013.01); *G01N 21/274* (2013.01); *G01N 21/65* (2013.01)

(58) Field of Classification Search
CPC .................................................. G01N 21/658
(Continued)

(56) References Cited

U.S. PATENT DOCUMENTS 2,393,620 A 10/1943 Adams et al.
4,659,676 A 4/1987 Rhyne, Jr.
(Continued)

FOREIGN PATENT DOCUMENTS

EP 2 755 031 A2 7/2014
GB 2 484 826 A 4/2012
(Continued)

OTHER PUBLICATIONS

International Search Report, dated Jan. 29, 2016, from corresponding PCT application.
(Continued)

*Primary Examiner* — Tarifur R Chowdhury
*Assistant Examiner* — Omar H Nixon
(74) *Attorney, Agent, or Firm* — BakerHostetler (57) ABSTRACT

An identification method, for determining whether a sample of an unknown composition is a sample of a known composition to which a known amount of a SERS-active taggant compound has been added, includes the steps of: obtaining a sample of the unknown composition; adding to the composition a plurality of SERS particles to form a mixture, each SERS particle including:—a core including a nanoparticle having a plasmonic surface,—a SERS-active internal standard compound adjacent the plasmonic surface and,—a shell, the shell encapsulating the core and the SERS-active internal standard compound; obtaining a SERS spectrum from the mixture; and comparing the SERS response ratio SATC:SAISC from the SERS spectral response of the SERS-active taggant compound and the SERS spectral response of the SERS-active internal standard compound in the unknown composition with the SERS response ratio SATC:SAISC from the known composition.

20 Claims, 2 Drawing Sheets

(58) Field of Classification Search
USPC .......................................................... 356/301
See application file for complete search history.

(56) References Cited

U.S. PATENT DOCUMENTS

| | | | |
|---|---|---|---|
| 4,735,631 A | 4/1988 | Orelup | |
| 5,358,873 A | 10/1994 | Nowak | |
| 9,618,454 B2* | 4/2017 | Marchant | B82Y 15/00 |
| 2006/0054506 A1 | 3/2006 | Natan et al. | |
| 2007/0165219 A1 | 7/2007 | Natan et al. | |
| 2010/0105026 A1* | 4/2010 | Bruckl | B82Y 15/00 |
| | | | 435/5 |
| 2010/0233816 A1 | 9/2010 | Natan et al. | |
| 2012/0057165 A1* | 3/2012 | Natan | G01N 33/532 |
| | | | 356/445 |
| 2012/0081703 A1* | 4/2012 | Moskovits | G01N 21/658 |
| | | | 356/301 |
| 2013/0045877 A1* | 2/2013 | Yap | G01N 33/54346 |
| | | | 506/7 |
| 2013/0271758 A1* | 10/2013 | Marchant | B82Y 15/00 |
| | | | 356/301 |
| 2014/0106469 A1* | 4/2014 | Wu | G01N 33/54346 |
| | | | 436/501 |

FOREIGN PATENT DOCUMENTS

| | | |
|---|---|---|
| WO | 2008/019161 A2 | 2/2008 |
| WO | 2010/057212 A1 | 5/2010 |
| WO | 2012/052779 A1 | 4/2012 |

OTHER PUBLICATIONS

GB Search Report, dated Mar. 20, 2015, from corresponding GB application.
GB Search Report, dated Mar. 17, 2016, from corresponding GB application.

* cited by examiner

ANALYTICAL METHOD USING SURFACE ENHANCED RAMAN SPECTROSCOPY AND COMPOSITION FOR THE METHOD

FIELD OF THE INVENTION

The present invention concerns a method of analysing a composition. More particularly the invention concerns determining the presence or absence of a compound in a material, especially the presence or absence of a taggant compound which has been added to material for the purposes of identification. In a particular form the present invention concerns quantitative or semi-quantitative analysis of a composition, especially for the determination of the quantity of a compound in a material for the purpose of identifying the material and assessing the likelihood of the material having been changed from its original composition.

BACKGROUND OF THE INVENTION

The use of various compounds as markers or taggants for liquid and solid materials is well known. Fluorescent dyes have been used in many applications, the fluorescence characteristics of a sample of the marked material being used to determine the presence and concentration of the taggant in the material. Other known taggants include biological compounds, especially DNA and oligonucleotides, and also phosphors. A typical application of these taggants is in the tagging of liquids such as hydrocarbon fuels in order to identify the liquid at a subsequent point in the supply chain. This may be done for operational reasons, e.g. to assist in distinguishing one grade of fuel from another, or for other reasons, in particular to ensure fuel quality, deter and detect adulteration and to provide a means to check that the correct tax has been paid. Apart from fuels, many other products, such as pharmaceuticals, agrochemicals, cosmetics, perfumes for example, may be marked to identify a product produced at a particular source, which may be certified to a particular standard or branded as an original high value product or for other purposes.

The problem of providing taggants which are difficult to reproduce by unauthorised persons yet readily identifiable and quantifiable by authorised persons has been addressed in many ways. Some prior methods involve the separation of the marker compound from the liquid by means of extraction into a polar liquid or onto a solid absorbent. For example, U.S. Pat. No. 5,358,873 describes and claims a method of detecting gasoline adulteration by tagging with a rhodamine dye and then shaking a small sample of the suspected fuel in a vial containing a small quantity of un-bonded flash chromatography-grade silica. The presence of the rhodamine marker dye in the suspect sample colours the silica red. U.S. Pat. No. 4,659,676, U.S. Pat. No. 2,392,620, and U.S. Pat. No. 4,735, 631 describe other methods for fuel marking and analysis.

DNA has been described for use as a taggant for various products, however the quantitative detection of nucleic acids, for example using hybridisation or quantitative PCR methods, is not sufficiently reproducible to encourage its use as a marker for products where detection of dilution or adulteration by detection of relatively small differences in the concentration of the taggant is required.

SERS (Surface Enhanced Raman Spectroscopy) is an analytical method in which the surfaces of certain metals enhance the Raman spectrum of compounds adsorbed onto or located in close proximity to such surfaces. The effect is sometimes referred to as a plasmonic effect and the surfaces may be referred to as plasmonic surfaces. Well-known plasmonic materials include gold, silver and copper. Compounds which exhibit such an enhancement in their Raman signal are referred to as "SERS-active" compounds. The enhancement of the Raman spectrum may be used to detect SERS-active compounds when they are present at concentrations at which they would not be detectable by other methods, for example non-enhanced Raman spectroscopy. The plasmonic effect is increased when a SERS-active compound is close to more than one surface. For that reason, plasmonic surfaces tend to be rough or regularly contoured. Alternatively when SERS is carried out using colloidal nanoparticles of plasmonic materials, the plasmonic effect, and therefore the SERS enhancement, is increased by aggregation of the colloidal particles so that molecules of the SERS-active compound may benefit from proximity to two or more particles. When we refer to SERS in the present specification we intend to include other forms of surface enhanced spectroscopy (SES) such as SERRS (surface-enhanced resonance Raman spectroscopy). For brevity these methods will all be referred to as SERS.

WO2008/019161 describes a method of fuel identification with surface enhanced Raman spectroscopy (SERS) tags. This method includes the association of a substance having a known Raman spectrum with a quantity of fuel. In one embodiment, a nanoparticle including a SERS active core may be mixed into a fuel supply. In an alternative embodiment, a SERS active dye including a Raman active reporter molecule may be mixed with a quantity of fuel. If the quantity of fuel is tagged with a Raman-active dye, the process of identifying the quantity of fuel may include mixing into a sample of the fuel a colloid of Raman enhancing metal particles and then acquiring the Raman spectrum of the Raman active reporter molecule associated with the tag. Suitable metals include, but are not limited to, silver or gold. Alternatively, a portion of the sample may be associated with a SERS active substrate. Although a semi-quantitative example of the procedure is described in WO2008/019161, we have found that the SERS response of the tags tends to vary such that the results include a significant uncertainty due to non-reproducibility. WO2012/052779 describes an improved method of detecting a taggant quantitatively by use of an internal standard in a particular way. Further improvements in the field are still desirable.

SUMMARY OF THE INVENTION

According to the invention, we provide a SERS particle comprising a solid core having a plasmonic surface, a SERS-active compound and a shell, said shell encapsulating said solid core and said SERS-active compound; characterised in that said solid core comprises an anisotropically-shaped nanoparticle.

DETAILED OF THE PREFERRED EMBODIMENTS

According to the invention, we further provide a method of estimating the concentration of a SERS-active analyte compound (SAAC) in a composition comprising the steps of:
  a) obtaining a sample of said composition;
  b) contacting said sample with a plurality of SERS particles, each SERS particle comprising:
     i. a core comprising a nanoparticle having a plasmonic surface, ii. a SERS-active internal standard compound (SAISC) adjacent said plasmonic surface and iii. a shell, said shell encapsulating said core and said SERS-active internal standard compound;

c) obtaining a SERS spectrum from the sample in contact with the SERS particles;

d) calculating the SERS response ratio SAAC:SAISC from the SERS response of the SERS-active analyte compound and the SERS response of the SERS-active internal standard compound.

In this description, the following abbreviations may be used:

SERS-Active Analyte compound: abbreviated to SAAC;

SERS-Active Internal Standard Compound: abbreviated to SAISC;

SERS-Active Taggant Compound: abbreviated to SATC.

By "nanoparticle" we mean a single particle having a maximum physical dimension (e.g. length, diameter etc.) in the range from 1 to 100 nm. The SERS nanoparticles may be any shape capable of being produced. In particular the SERS nanoparticles may be shaped in the form of a rod, prism, star, cube or ellipsoid. SERS (plasmonic) enhancement of molecules may be greater when the molecule is in proximity to more than one plasmonic surface. The SERS nanoparticle may be non-spherical. The nanoparticulate core of the SERS particle may be shaped in the form of a rod, prism, star, cube, sphere, nanoflower, nanoshell, nanocage, hollow nanospheres, nanodentrite, nanourchin, tetrahedron, hexahedron, octahedron, icosahedron and dodecahedron, triangle, polygonal plate or trigonal prism. One particular embodiment of the invention may include a rod-shaped nanoparticle core.

The core has an outer surface which is capable of enhancing the Raman scattering of a SERS-active compound. The outer surface of the core may comprise any known SERS-enhancing material. The surface of the core may comprise gold, copper, silver or a mixture or alloy thereof. The use of other plasmonic surfaces, particularly metals, may be possible, including Na and Al and transition metals such as Pt, Ni, Ru, Rh, Pd, Os, Co, Fe and Cr. As new methods of surface-enhanced spectroscopy are developed, different SES-promoting surfaces may become available and may be useful. The core may consist of a nanoparticle formed of the same material as the surface, i.e. the core may comprise a solid nanoparticle. The solid nanoparticle may comprise gold, copper, silver or a mixture or alloy thereof. Alternatively the core may comprise at least two different materials: a material having a plasmonic surface at the outer surface of the core and a different material inside the outer surface of the core. The SERS particle may contain more than one core nanoparticle. The core may be hollow, i.e. the core may comprise a material enclosing a void space.

The SERS particle may comprise either one or more than one core. The SERS particle may contain a plurality of cores which are arranged in a regular manner, for example the cores may be aligned with each other. Alternatively the SERS particle may contain an aggregation or cluster of core nanoparticles.

The shell may be formed from an organic or an inorganic material. Inorganic materials suitable as shell materials include glass, silica and metals, such as Ti and Zr. Organic shell materials may include polymers, for example acrylic polymers such as polyacrylic acid and functionalised derivatives thereof; vinyl polymers such as polystyrene and functionalised derivatives thereof; polyamides, including naturally derived polymers such as polypeptides and salts thereof; polyesters and functionalised derivatives thereof, including naturally derived polyesters; and polyols, such as polyethylene glycol. Some examples of suitable polymers include poly(acrylic acid and salts thereof, poly-L-glutamic acid and salts thereof, poly(allylamine hydrochloride, poly-L-lysine hydrochloride, poly(4-styrenesulfonic acid and salts thereof and poly(diallyldimethylammonium chloride) Salts of these polymers include any suitable counter-ion; often the sodium salt is used. A polymeric shell may be formed by polymerisation of at least one suitable monomer in admixture with the nanoparticle cores and SERS active internal standard to form a polymeric shell layer in situ. Alternatively a solution or dispersion of a polymer may be mixed with the nanoparticle cores and SERS active internal standard and treated, e.g. by removal of solvent, to deposit a layer of polymer around the nanoparticle cores and SERS active internal standard. A dissolved or dispersed polymer may be attracted to a core/internal standard combination and deposit to form a shell layer by suitable selection of a polymer functional group. For example, a negatively charged polymer (e.g. including a carboxylate or sulphonate group) may be attracted to a positively charged core/internal standard combination. More than one shell material may be present.

The shell surrounds the core and SERS-active internal standard compound so that the core and SERS-active internal standard compound are encapsulated within the shell. The encapsulation of the core and SERS-active internal standard compound by the shell provides a stable SERS particle which may be stored over an extended period of time without affecting the SERS spectrum obtained from the SERS-active internal standard compound. This is achievable because the shell protects the core and SERS-active internal standard compound from environmental effects, such as oxidation. The shell may provide such protection for a period of months or years, in order to provide a SERS particle with a long "shelf-life". In some applications the shelf-life may be required to be no more than days or weeks. The shell may be permeable to some molecules. The shell preferably does not induce aggregation of the nanoparticles to an extent which materially affects the method of the invention or the preparation of the SERS particles. In some embodiments, a shell material may be selected which does not have a strong SER(R)S signal at the excitation wavelength used to measure the SAISC and SAAC. The shell material may be transparent to the excitation wavelength used to obtain a SERS response from the SAISC, so that the excitation light is capable of interacting with the SAISC. The shell may interact with the SAISC to produce a reproducible and measurable SERS response.

The SERS-active internal standard compound (SAISC) may be selected from a wide range of chemical compounds. The SAISC may be selected to provide a measurable SERS response at the excitation wavelength used to obtain a SERS response from the SAAC. Such a response is preferably readily reproducible. The selection of SERS-active internal standard compound (SAISC) may be influenced by the nature of the SERS-active analyte compound (SAAC) in the composition.

The SAISC may have a SERS spectrum containing at least one band which is distinguishable from all of the bands in the SERS spectrum of the SAAC upon excitation by the same excitation wavelength. The SAAC may have a SERS spectrum containing at least one band which is distinguishable from all of the bands in the SERS spectrum of the SAISC upon excitation by the same excitation wavelength. In this way, the SERS response of the composition contains individual bands which are attributable to the SAISC and to the SAAC. When the SERS spectra of the SAISC and SAAC have overlapping bands then it may be possible to distinguish the response of the SAAC and the SAISC by using spectrum analysis software. The SERS response of the SERS-active analyte compound and the SERS response of the SERS-active internal standard compound may be determined by exciting the molecules at different wavelengths. It is preferred that the SAAC does not produce significant or measurable fluorescence at the wavelength used to obtain its SERS spectrum. The SERS nanoparticle may comprise >1 SERS-active internal standard.

The SERS active internal standard compound may comprise the shell material. The shell material may contain one or more chemical groups which give a measurable SERS response which can be used as the SAISC. When the shell material includes or comprises the SAISC, the SERS particle may or may not comprise an additional SAISC. The shell material may comprise the SAISC, for example in the form of a SERS-active chemical group which is an integral part of the shell material, bound to the shell material or physically mixed with the shell material.

The SAISC may comprise a stabilising agent for the nanoparticle. The SAISC preferably interacts with a stabilising agent or surfactant. Such interaction may facilitate encapsulation of the SAISC and core. The SAISC preferably does not induce aggregation of the nanoparticles to an extent which materially affects the method of the invention or the preparation of the SERS particles.

The SERS particles, comprising a core, SAISC and shell may comprise a surfactant, or stabilising agent, which is present between the external surface of the core and the shell. The surfactant may be a cationic surfactant, such as cetyltrimethylammonium bromide (CTAB), octadecyl-p-vinylbenzyldimethylammonium chloride, tetradecyl trimethylammonium bromide (TTAB) and benzyldimethylhexadecylammoniumchloride (BDAC). The surfactant may alternatively be an anionic surfactant or a non-ionic surfactant, such as Tween® 20 (polyoxyethylene 20), The surfactant may be a surfactant which is used to create colloidal metal nanoparticles forming the core of the SERS particle. The surfactant molecules are believed to orient themselves relative to the external surface of the core in a particular way. The orientation of the surfactant molecules is believed to contribute to the regular orientation of SAISC molecules with respect to the external surface of the core. The plasmonic enhancement of the Raman spectrum obtained from a molecule is dependent on the orientation of the molecule with respect to the plasmonic surface. When the molecules of the internal standard compound are preferentially or predominantly oriented in the same direction, the SERS spectrum may be more reproducible compared with the spectrum obtained from randomly oriented molecules. The presence of surfactant between the core and the shell therefore contributes to enhancing the SERS response of the internal standard and maintaining that response in a stable manner.

The surfactant may enable or promote interaction between the SAISC and the core and/or between the SAISC and the shell. If the surfactant has a measurable SER(R)S signal at the excitation wavelength used to measure the SAISC and SAAC then appropriate steps such as the use of spectrum analysis software, may be required to prevent such a signal from interfering with the measurement of the SERS response of the SAISC and SAAC. It is preferred to use a surfactant which does not have a strong SER(R)S signal at the excitation wavelength used to measure the SAISC and SAAC. The surfactant, or stabilising agent, may interact with the SAISC to produce a reproducible and measurable SERS response.

The surfactant material may comprise the SAISC, for example in the form of a SERS-active chemical group bound to the surfactant or physically mixed with it.

The presence of a surfactant in the SERS particle may provide a means by which the spacing of the internal standard from the metal surface may be controlled. When the encapsulating shell has a controlled thickness it is possible to control the spacing of the SAAC or SATC from the metal surface, The spacing of the SAAC from the plasmonic surface may be controlled to bring the SAAC sufficiently close to the plasmonic surface for SERS to be possible and to bring a large proportion of such SAAC molecules to within a predetermined distance of the plasmonic surface.

The SERS particle may comprise a polymerisable surfactant, The polymerisable surfactant may be present both as a stabiliser for the SAISC and, in its polymerised form, as a shell material. An example of a suitable polymerisable surfactant is 11-(acryloyloxy)undecyltrimethylammonium bromide.

The thickness of the shell may affect the extent of the effect of the plasmonic surface of the core on the enhancement of the Raman scattering of the SERS-active analyte because the thickness of the shell affects the distance between the surface of the core and the SERS-active analyte. The distance between the surface of the core and the external surface of the shell may be in the range 1-15 nm. In preferred embodiments the distance between the surface of the core and the external surface of the shell may be in the range 1-12 nm, especially 1-5 nm. The distance may be <10 nm. It is preferred that the shell thickness is reproducibly similar between similar SERS particles.

The shell may include functional portions which are capable of interacting with chemical compounds. The functional portion may include functional groups such as amines, alcohols, thiols, carboxylic acids, sulfonic acids and salts of such acids. When a functional portion is present on the external surface of the shell, the SERS particle may interact with a chemical compound in the sample of composition to which it is added. The SERS particle may interact with a chemical compound in the composition in such a way that the chemical compound is bound to, or incorporated into, the external surface of the shell. The term "bound" here includes but is not limited to physical, electrostatic and chemical binding. The terms "binding", "bind", "bonded", "bond" and "bonding" should be interpreted in a similar manner. The chemical compound may be absorbed, adsorbed, bonded by means of covalent, ionic or co-ordinate bonding or magnetically bonded. The shell may include functionalised portions which are selected to interact with the SERS-active analyte compound in the composition. The shell may include functionalised portions which are selected to bind preferentially to the SERS-active analyte compound in the composition. When the functionalised portion is selected to bind preferentially to the SERS-active analyte compound in the composition, the SAAC is held in proximity to the SERS particle and is influenced by the plasmonic surface of the core such that a SERS spectrum is obtainable from the SAAC. The shell may interact with the SAAC by being or becoming selectively permeable to the SAAC (or SATC). Functionalised portions of the shell may provide selective permeability of the shell to the SERS-active analyte compound in the composition. A functionalised shell may therefore bring a compound closer to the surface of the core than an unfunctionalised shell may do. The nature of the functional group(s) included in the functionalised portion of the shell material may be selected to be compatible with the particular analyte of interest. When the SAAC is a taggant compound (SATC), the SATC and complementary SERS particles including a functionalised portion which binds specifically to the SATC, may be supplied as a matched system for marking and identifying a product. The supply of such a system may provide an increasing level of complexity to the tagging of products which may deter the manufacture of counterfeit products. A functionalised portion may be included in the shell by forming the shell from a functionalised material. For example, a suitable shell polymer containing a functionalised portion may be formed by polymerisation of a functionalised monomer or by functionalising a formed polymer by reaction with a compound containing the required functionality.

The SERS-active analyte compound may be a taggant (SERS-Active Taggant Compound (SATC)), i.e. a compound which is added to the composition for the purpose of providing a means by which the composition may be subsequently identifiable. An identification method, according to the invention, for determining whether a sample of an unknown composition is a sample of a known composition to which a known amount of a SERS-active taggant compound (SATC) has been added, therefore comprises the steps of:
  a) obtaining a sample of said unknown composition;
  b) contacting said sample with a plurality of SERS particles, each SERS particle comprising:
    i. a core comprising a nanoparticle having a plasmonic surface,
    ii. a SERS-active internal standard compound (SAISC) adjacent said plasmonic surface and
    iii. a shell, said shell encapsulating said core and said SERS-active internal standard compound;
  c) obtaining a SERS spectrum from sample in contact with said SERS particles comparing the SERS response ratio SATC:SAISC from the SERS spectral response of the SERS-active taggant compound and the SERS spectral response of the SERS-active internal standard compound, in the sample of unknown composition with the SERS response ratio SATC:SAISC from said known composition.

When a known concentration of a SERS-active taggant compound (SATC) has been added to a known composition, it may be possible to detect later adulteration of the known composition by measuring the concentration of the SATC in a sample of a similar composition which is analysed after the opportunity for adulteration has occurred. For example, if the composition is a branded product such as a perfume, it may be labelled by adding a small quantity of a SATC, i.e. an identifiable compound, at a known concentration. The perfume may then be distributed through the usual supply chain. A sample of a similarly branded product may later be obtained and analysed to determine whether it is a sample of the product to which the SATC was added. The sample of the product (i.e. the composition) may then be analysed by the method of the invention to determine whether the SATC is present, and, if present, its concentration. If the SATC is not detected, then it may be inferred that the sample is not a sample of the composition to which the SATC was added and that it may not, therefore be a sample of a genuine product. If the SATC is present but in a significantly different concentration from the concentration at which it was added to the composition then it may be inferred that the product from which the sample was taken may have been changed, either by dilution or by concentration of a portion of the composition.

The method may be used to identify compositions which are liquid or solid. If the composition is a solid, then it may be dissolved in a solvent prior to analysis using the method of the invention. The method is suitable for identifying a variety of types of compositions, including organic liquids, water, aqueous solutions, powdered solids, particulate solids, solid objects or a plurality of objects. Examples of materials for which the method of the invention may be desirably practised, include hydrocarbons, petrochemicals, fuels, mineral oils, vegetable oils, liquids that are known to be used to adulterate fuels and oils such as organic solvents, alcohols, diesel exhaust fluids, pharmaceuticals, agrochemicals, cosmetics, perfumes and other high value or highly-taxed products. The composition or material may be dissolved or dispersed in a liquid before analysis if required. This is especially useful if the material is a solid but may also be used for liquid or semi-liquid materials.

The SATC is a compound which does not interfere with the intended use or quality of the composition. If the composition is intended as a medicament, cosmetic or perfume for example, the SATC should be non-toxic at the concentration at which it is present. The SATC may produce a visible change in the composition, e.g. it may be coloured. Usually the taggant is not visible in the composition at the concentration at which it is used. When the composition to be marked is a liquid, the SATC is preferably soluble in the liquid which is to be marked with the SATC up to the concentration which is to be used. The SATC is preferably soluble in the liquid up to a concentration which is measurable using SERS analysis. The SATC may be less soluble in the material to be marked than it is in a solvent used to extract it prior to SERS analysis. When the material is a solid, the SATC may be a solid compound which is mixed with or coated onto the material. When the material is analysed, the SATC may be dissolved or extracted into the composition which is analysed by the method of the invention.

The SAAC is a chemical compound which can be identified by its Raman signal when in close proximity to or contact with a SERS substrate. In the identification method of the invention the SAAC is a taggant, i.e. an SATC. The taggant is SERS-active, i.e. it produces a Raman spectrum when in proximity to a plasmonic Raman-enhancing substrate.

We have found that chemical compounds suitable for use as the SAAC (or SATC) or SAISC may be selected from neutral, cationic, anionic or zwitterionic organic compounds. The chemical compounds may contain at least 1 aromatic or unsaturated hydrocarbon region. An aromatic hydrocarbon region may comprise one or more 4, 5, 6, or 7-membered unsaturated or fused rings containing 0, 1 or more heteroatoms. The aromatic region may be selected from the group consisting of pyrolyl, pyrimidinyl, pyridyl, benzyl, triazinyl, pyrazolyl, triazolyl, tetrazolyl, tetrazinyl units. The aromatic region may be further functionalised with 0, 1 or more groups, including linear or cyclic alkane, alkene, alkynes, nitro, nitrile, alcohol, ether, ester, amide, aldehyde, thiol, thioether, amine, halide, sulphide, cyanate, carboxylic acid, ketone, sulfone, sulfoxide, sulfonic acid, phosphonic acid or phosphine. The SAAC and/or the SAISC may comprise a dye. The SAAC and/or the SAISC may comprise a non-dye compound. The SAAC and/or the SAISC may be selected from dyes such as anthraquinone, azo, azin, azine, cyanine, ruthenium, fluorescent dyes, arylmethane, coumarins, natural dyes, diarylmethane, triarylmethane, xanthene, acridine, sulphur dyes, diazonium, naphthol, nitro, nitroso, phthalocyanine, squarine, quinone-imine (azin, eurhodin, safranin), indamine, indophenol, indigo, peryelene, phenol, oxazin, oxazone, thiazine, thiazole, xanthene, fluorene (pyronin), rhodamine, fluorine, quinolone, violanthrone, solvent dyes, acid dyes, basic dyes, disperse dyes, heptamethine dyes, mordant dyes, staining dyes, vat dyes and reactive dyes. Selected dye molecules may be positively charged, negatively charged or neutral.

Examples of suitable dye compounds include Fast green FCF, Victoria Blue R, Victoria Blue B, N,N-dimethylindoaniline, Sudan Orange G, Rhodamine B, Rhodamine B isothiocyanate, Rhodamine B base, Rhodamine 800, Rhodamine 6G, Rhodamine 530, Rhodamine 110, Pthalocyanine, Erythrosin B, 9,10-dibromophenanthrene, Celestine Blue, Gallocyanine, IR125, IR1061, IR1048, IR26, IR144, IR140, Eosin Yellowish, pyrromethane 597, Oil Red O, Alizarin Red S sodium salt, Perylene-3,4,9,10-tetracarboxylic dianhydride, Methylene blue, Methylene blue hydrate, Basic blue 41, Disperse Blue 79, Bromocresol purple, Bromocresol green, Bromophenol blue, Cresyl violet acetate, Red 462, Oxazine 725 tetrafluoroborate, Oxazine 725 perchlorate, Toluidine blue, Toluidine blue O, Coumarin 6, Coumarin 460, Comarin 334, Coumarin 540A, Solvent Blue 59, Pyranine, dimethyl yellow, 1,3,6,8-Pyrenetetrasulfonic acid tetrasodium salt hydrate, crystal violet, 3,3'-dibutylthiacarbocyanine, fluoroscein disodium salt hydrate, Indigo, Sudan Black B, Sudan II, 1,1-diocatdecyl-3,3,3',3'-tetramethylindocarbocyanine perchlorate, Erioglaucine disodium salt, 3-(2-Benzothiazolyl)-7-(diethylamino)coumarin, sulforhodamine B monosodium salt, Dimethyl popop, Orange OT, Allure Red AC, Malachite Green, Fast green FCF, N,N-dimethylindoaniline, Pthalocyanine, Erythrosin B, 9,10-dibromophenanthrene, Celestine Blue, Indoline dye D149, 2,6-Diphenyl-4-(2,4,6-triphenyl-1-pyridinio)phenolate, Methyl Orange, Acid Red 27, Congo Red, indigo carmine, alizarin, purpurin, Acid Yellow 23, Safranin O, Basic Fuchsin, Brilliant Green, 3-Amino-7-dimethylamino-2-methylphenazine hydrochloride, 1-phenylazo-2-naphthol-6,8-disulfonic acid disodium salt, 2-Cyano-3-[5'''-(9-ethyl-9H-carbazol-3-yl)-3',3'',3''',4-tetra-n-hexyl-[2,2',5',2'',5'', 2''']-quater thiophen-5-yl] acrylic acid, Ruthenate(2-), [[2, 2'-bipyridine]-4,4'-dicarboxylato(2-)-$N^1,N^{1'}$][4,4'-bis[5-(hexylthio)-2-thienyl]-2,2'-bipyridine-$N^1,N^{1'}$]bis (thiocyanato-N)-, cis-Bis(isothiocyanato)(2,2'-bipyridyl-4, 4'-dicarboxylato)(4,4'-bis(5-(hexylthio)thiophen-2-yl)-2,2'-bipyridyl)ruthenium(II), 2',4',5',7'-tetrabromo-4,5,6,7-tetrachlorofluorescein disodium salt, 4,4'-(imidocarbonyl) bis(N,N-dimethylaniline) monohydrochloride, Merocyanine 540, 2,3,6,7-tetrahydro-9-(trifluoromethyl)-1H,5H,11H-[1] benzopyrano(6,7,8-ij)quinolizin-11-one, 3-(2-N-methylbenzimidazolyl)-7-N,N-diethylaminocoumarin, 2,3,6,7-tetrahydro-9-methyl-1H,5H-quinolizino(9,1-gh)coumarin, Light Green SF Yellowish, 4,4'-(m-phenylenebisazo)bis-m-phenylenediamine dihydrochloride, cobalt(II) phthalocyanine, 2',4',5',7'-tetrabromoeosin ethyl ester potassium salt, 4,5,6, 7-tetrachloro-2',4',5',7'-tetraiodofluorescein sodium salt, 10,11,14,15-tetrahydro-6-imino-9,9,15,15-tetramethyl-6H, 9H,13H-benzimidaz[1'',2'':1',2']pyrido[4',3':2,3][1]benzopyrano[6,7,8-ij]quinolizine-7-carbonitrile, 3-butyl-2-[5-(3-butyl-1,3-dihydro-1,1-dimethyl-2H-benzo[e]indol-2-ylidene)-penta-1,3-dienyl]-1,1-dimethyl-1H-benzo[e] indolium perchlorate, 2-[5-[3,3-dimethyl-1-(4-sulfobutyl)-1,3-dihydro-indol-2-ylidene]-penta-1,3-dienyl]-3,3-dimethyl-1-(4-sulfobutyl)-3H-indolium hydroxide, inner salt, sodium salt, 1-butyl-2-[5-(1-butyl-1H-benzo[cd]indol-2-ylidene)-penta-1,3-dienyl]-benzo[cd]indolium tetrafluoroborate, 5-(2-(2-(5-chloro-1-ethyl-3,3-dimethyl-3H-indolium-2-yl)vinyl)-5-(2-(5-chloro-1-ethyl-3,3-dimethylindolin-2-ylidene)ethylidene)cyclopent-1-en-1-yl)-1,3-dimethyl-2,6-dioxo-1,2,3,6-tetrahydropyrimidin-4-olate, 1,3-dimethyl-2,6-dioxo-5-(2-(2-(1,3,3-trimethyl-3H-indolium-2-yl)vinyl)-5-(2-(1,3,3-trimethylindolin-2-ylidene)ethylidene)cyclopent-1-en-1-yl)-1,2,3,6-tetrahydropyrimidin-4-olate, 6-butoxy-2-[5-(6-butoxy-1-butyl-1H-benzo[cd]indol-2-ylidene)-penta-1,3-dienyl]-1-butyl-benzo[cd]indolium tetrafluoroborate, 2-[3-chloro-5-(1,3,3-trimethyl-1,3-dihydro-indol-2-ylidene)-penta-1,3-dienyl]-1,3,3-trimethyl-3H-indolium chloride, 1-butyl-2-[5-(1-butyl-1,3-dihydro-3,3-dimethyl-2H-indol-2-ylidene)-penta-1,3-dienyl]-3,3-dimethyl-3H-indolium perchlorate, 1-butyl-2-(2-[3-[2-(1-butyl-3,3-dimethyl-1,3-dihydro-indol-2-ylidene)-ethylidene]-2-chloro-cyclohex-1-enyl]-vinyl)-3, 3-dimethyl-3H-indolium hexafluorophosphate, 1,3-bis[4-(diethylamino)-2-hydroxyphenyl]-2,4-dihydroxy-cyclobutenediylium bis(inner salt), 1,3,3-trimethyl-2-[5-(1, 3,3-trimethyl-1,3-dihydro-indol-2-ylidene)-penta-1,3-dienyl]-3H-indolium chloride, 1-butyl-2-[5-(1-butyl-3,3-dimethyl-1,3-dihydro-indol-2-ylidene)-3-chloro-penta-1,3-dienyl]-3,3-dimethyl-3H-indolium hexafluorophosphate, 2-[2-[2-chloro-3-[2-(1,3-dihydro-1,3,3-trimethyl-2H-indol-2-ylidene)-ethylidene]-1-cyclohexen-1-yl]-ethenyl]-1,3,3-trimethyl-3H-indolium tetrafluoroborate, 1,3-dihydroxy-2, 4-bis(2,3,6,7-tetrahydro-8-hydroxy-1,1,7,7-tetramethyl-1H, 5H-benzo[ij]quinolizin-9-yl)-cyclobutenediylium bis(inner salt), 3-butyl-2-[5-(3-butyl-1,3-dihydro-1,1-dimethyl-2H-benzo[e]indol-2-ylidene)-3-chloro-penta-1,3-dienyl]-1,1-dimethyl-1H-benzo[e]indolium hexafluorophosphate, 2-[5-[1, 1-dimethyl-3-(3-methyl-butyl)-1,3-dihydro-benzo[e]indol-2-ylidene]-penta-1,3-dienyl]-1,1-dimethyl-3-(3-methyl-butyl)-1H-benzo[e]indolium hexafluorophosphate. Dyes may be used in the form of salts or other stabilised forms thereof and the most appropriate form will be selected by the skilled person to be stable in the composition.

In the method described in WO2012/052779, the taggant must also be available as an isotopically-altered version for use as an internal standard in the method. The use of an isotopically altered version of the taggant as internal standard was intended to ensure that the adsorption properties of the standard and the taggant to aqueous colloidal nanoparticles were as similar as possible. In the method of the present invention, the SAISC may not be an isotopically-altered version of the SAAC (including where the SAAC is a taggant). This allows a greater selection of compounds to be used as internal standards for the method of the invention. A further advantage is that the method of the present invention facilitates the use of multiple SATCs for tagging a composition.

It is preferred that the SATC and the SAISC are selected to exhibit no or low fluorescence at the excitation wavelengths used to obtain their Raman spectra. It is, however, known that proximity to a plasmonic surface may quench fluorescence, at least to some extent, so some level of fluorescence may be tolerated.

The use of a SERS-active compound as a taggant enables the taggant to be identified at very low concentration. The taggant may be present at a concentration of 1 ppt (parts per trillion)-100 ppm (parts per million). The taggant may be present at a concentration of 50 ppt-1000 ppb (parts per billion). More than one SATC may be present. In case more than one SATC is present in the composition, each SATC may be selected to produce a SERS response at the same or different wavelength from the, or each, other SATC.

The SERS particles may be provided as a dispersion, for example a colloidal solution, in a fluid, usually an aqueous or organic liquid. In such a case, contact of the sample with the SERS particles may be effected by mixing the sample (or a portion thereof) with the SERS particles, either dispersed in a fluid or separated from such a dispersion, to form a mixture. The SERS spectrum may then be obtained from the mixture.

The SERS particles may be provided in a form in which they are localised on a surface. The SERS particles may be fixed to the surface for the duration of the method. Alternatively, the SERS particles may be provided in a form in which they are localised on a surface from which they detach when the method of the invention is carried out. Localising SERS particles on a surface may be achieved by printing a composition containing the SERS particles onto a surface of a substrate, for example by ink-jet printing; soaking a substrate in a dispersion of SERS particles followed by withdrawal of the substrate from the dispersion, or depositing the SERS particles on a surface of a substrate by spray deposition or any other appropriate method. The surface of the substrate carrying the SERS particles may optionally be dried, cured or otherwise treated.

The SERS spectrum may be obtained from the sample which is in contact with the SERS particles by known methods. The method requires the use of a suitable Raman spectrometer. The excitation energy may be provided by one or more lasers, optionally in combination with suitable filters. The calculation of the concentration of the SAAC (or SATC) and/or its comparison with a known concentration of a known taggant compound may be carried out using an electronic data processor. The data processor may be associated with the Raman spectrometer and may further be incorporated into the data processing facility of the Raman spectrometer. The data processor may comprise an apparatus which is separate from the Raman spectrometer. The data processor may comprise a computer, such as a portable computer or other electronic calculating device, such as a suitably programmed tablet computer or mobile device such as a telephone. The use of a portable or compact Raman spectrometer may be particularly useful if sample analysis is to be carried out in an environment where laboratory equipment is not generally available. For the identification method, where the concentration of a SERS-active taggant is to be established, it may be desirable for the analysis to take place at or near to the source of the sample, for example at a location where a product which is to be identified is distributed or used.

The concentration of the SERS-active analyte compound or SERS-active taggant compound may be calculated from the SERS response ratio SAAC:SAISC or SATC:SAISC, i.e. the ratio of a characteristic of the Raman spectroscopy detector response to the SAAC or SATC to the Raman spectroscopy detector response to SAISC. The detector response ratio may be the ratio of selected bands (for example band height or band area) of the respective SERS spectra. The calculated ratio SATC/SAISC may be compared with a reference value representing the SATC/SAISC from a reference sample containing a known concentration of SERS-active taggant compound. The SERS spectrum obtained from a reference sample containing only the target SERS-active taggant or the internal standard may be used to identify suitable bands which are characteristic of either the taggant or the internal standard, which may be selected for comparing the relative response of the compounds. The relative response may be calculated from the relative intensity of one band attributable to each compound or from more than one band. As an alternative, whole spectra, or portions thereof, may be compared. A calculated property of the spectrum, such as the relative response compared to a reference spectrum of one or each compound present, may be used to represent the detector response due to the SAAC, SATC or SAISC. It is not always necessary to collect and display an extended Raman spectrum. In the identification method of the invention, the identity of the SATC and SAISC are known, therefore it may be sufficient to measure the detector response at one or more predetermined Raman shift wavenumbers or ranges of wavenumbers and calculate a concentration of the taggant or analyte from the measured response. The result of the calculation may be displayed to the user as a concentration value, a "pass/fail" result or as an arbitrary value of quality or similarity based upon a value for a solution containing a standard amount of the taggant. Methods of comparing spectra and calculating relative response and ratios of the band intensities are well-known and are typically carried out using a suitable computer programmed with spectroscopic data handling software. The relationship between the concentration of the SERS-active taggant compound and the Raman detector response ratio may be determined by calibration.

SERS particles used in the method of the invention may be made by methods described in the literature. Suitable methods are described in A. W. Wark et al in Phys. Chem. Chem. Phys. (2013) 15, 18835-18843.

The invention will be further described in the following examples.

EXAMPLE 1

Preparation of SERS Particles

Gold nanorods were prepared via the seed-mediated method described by Sau et al (T. K. Sau, Murphy, C. J., Langmuir, 2004, 20, 6414-6420). The nanorods were centrifuged to remove excess reactants and re-suspended in 1 mM CTAB. A 10 mM solution of a SERS-active compound "A" as internal standard was added to the nanoparticles (present at 1.2 nM) to give a final internal standard concentration of 1 mM. The sample was left to equilibriate overnight. Following this, the samples were encapsulated by forming a shell using poly(styrene 4-sulfonate (sodium salt)) (PSS) by adding drop-wise, with stirring, 200 µl of 10 mg/ml PSS in 5 mM NaCl for every 1 ml of nanorods. The sample was then centrifuged three times to remove excess polymer, and resuspended in water.

EXAMPLE 2

Use of SERS Particles in the Method

Methanol was tagged with a SERS-active taggant compound (Compound "B") in water. The tagged solvents were then diluted with water from 0-100% dilution in 10% steps.

For each of the diluted tagged solvent samples, 240 µl of the SERS particles made in Example 1 were added to a vial, with 240 µl of tagged solvent. The samples were shaken by hand for 3 seconds and analysed by SE(R)RS at 785 nm excitation, with a laser power of 40 mW, and a 1 second accumulation time. In order to quantify the response, the area of selected bands from the spectrum of the SERS-active taggant compound and internal standard was determined, and the response was normalized as follows:

Normalized response=response of SATC molecule/response of SAISC.

Figure 1:
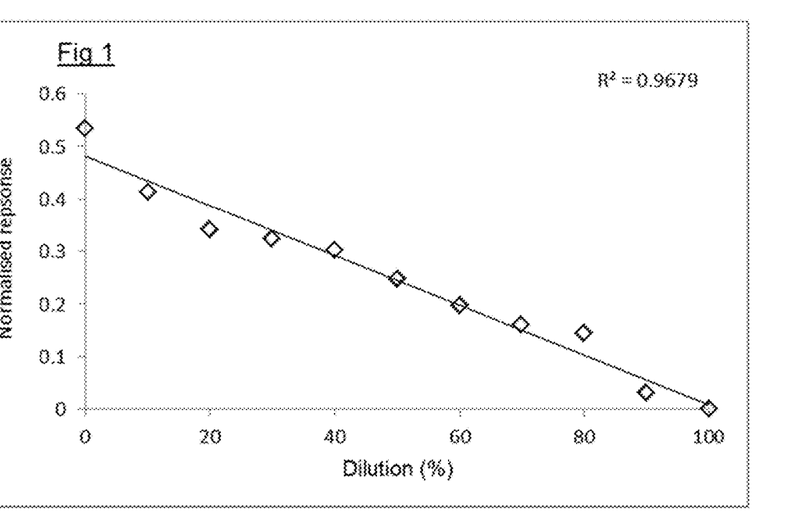

The normalised response was plotted against SATC dilution, and the $R^2$ value for each tagged solvent was determined as an indication of linearity between normalised response and dilution. The result is shown in FIG. 1, in which the markers are shown solely to indicate the location of a data point and are not intended to indicate any quantum of error.

EXAMPLE 3

Figure 2:
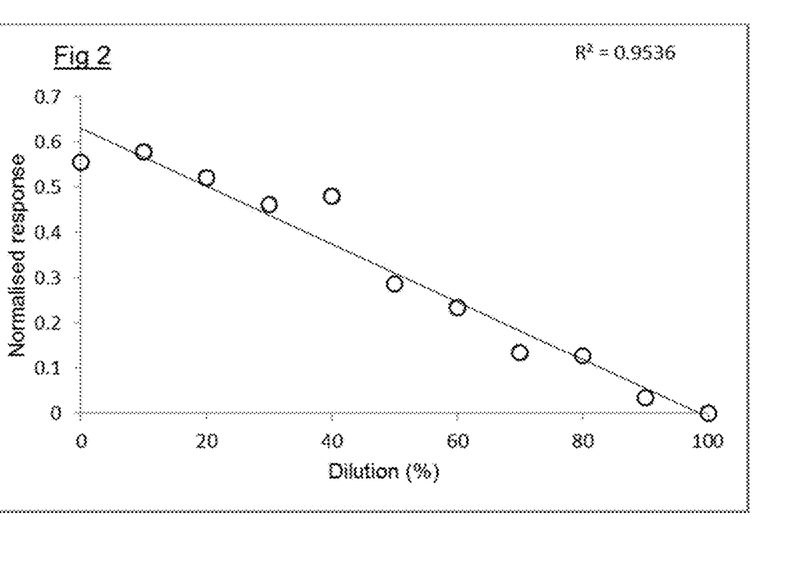

Example 2 was repeated using ethanol instead of methanol. The result is shown in FIG. 2.

The markers are not intended to indicate any error limits.

EXAMPLE 4

Figure 3:
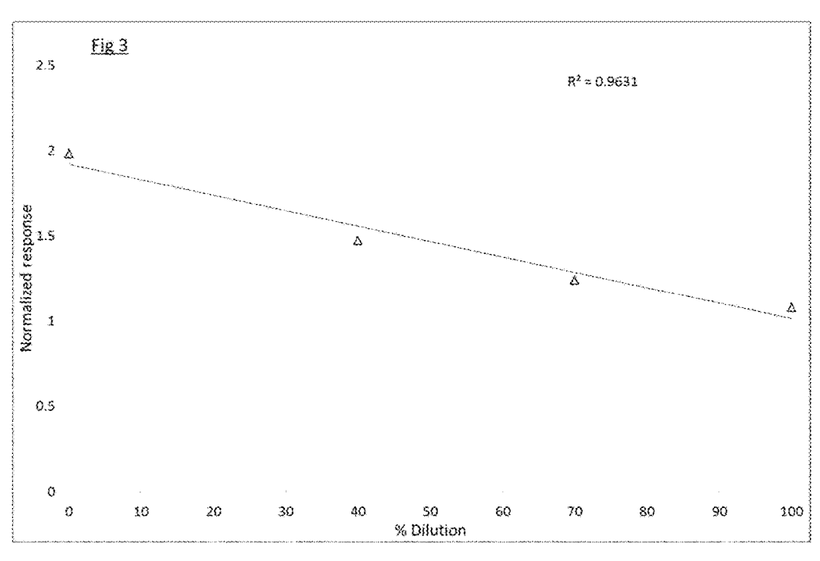

The method of Example 2 was carried out in a similar way, using a 32.5 wt % aqueous solution of urea, which is commercially used as a diesel exhaust fluid (DEF). The SERS-active taggant compound used was Compound C. Four dilutions of Compound C in the DEF were used and the response quantified from the peak height of selected peaks in the SERS spectrum and normalised against the response of the SAISC contained in the SERS particles, as described above, is plotted in FIG. 3.

The invention claimed is:

1. An identification method, for determining whether a sample of an unknown composition is a sample of a known composition to which a known amount of a SERS-active taggant compound has been added comprises the steps of:
   a) obtaining a sample of said unknown composition;
   b) adding to said composition a plurality of SERS particles to form a mixture, each SERS particle comprising:
      i. a core comprising a nanoparticle having a plasmonic surface,
      ii. a SERS-active internal standard compound adjacent said plasmonic surface, wherein the SERS-active internal standard compound is not an isotopically-altered version of the SERS-active taggant compound, and
      iii. a shell, said shell encapsulating said core and said SERS-active internal standard compound;
   c) obtaining a SERS spectrum from said mixture
   d) comparing the SERS response ratio SATC:SAISC from the SERS spectral response of the SERS-active taggant compound and the SERS spectral response of the SERS-active internal standard compound in the unknown composition with the SERS response ratio SATC: SAISC from said known composition.

2. An identification method according to claim 1, wherein said core nanoparticle is anisotropic.

3. An identification method according to claim 2, wherein said core nanoparticle is shaped in the form of a rod, prism, star, cube, sphere, nanoflower, nanoshell, nanocage, hollow nano sphere, nanodentrite, nanourchi, tetrahedron, hexahedron, octahedron, icosahedron and dodecahedron, triangle, polygonal plate or trigonal prism.

4. An identification method according to claim 2, wherein said shell includes functional portions which are capable of interacting with the SERS-active taggant compound.

5. An identification method according to claim 2, wherein the distance between the surface of the core and the external surface of the shell is in the range 1-15 nm.

6. An identification method according to claim 1, wherein said core nanoparticle is shaped in the form of a rod, prism, star, cube, sphere, nanoflower, nanoshell, nanocage, hollow nanosphere, nanodentrite, nanourchin, tetrahedron, hexahedron, octahedron, icosahedron and dodecahedron, triangle, polygonal plate or trigonal prism.

7. An identification method according to claim 6, wherein said shell includes functional portions which are capable of interacting with the SERS-active taggant compound.

8. An identification method according to claim 6, wherein the distance between the surface of the core and the external surface of the shell is in the range 1-15 nm.

9. An identification method according to claim 1, wherein said shell includes functional portions which are capable of interacting with the SERS-active taggant compound.

10. An identification method according to claim 9, wherein said functionalised portion comprises a positively charged moiety or a negatively charged moiety.

11. An identification method according to claim 1, wherein the distance between the surface of the core and the external surface of the shell is in the range 1-15 nm.

12. An identification method according to claim 1, wherein said SERS active internal standard compound may comprise the shell material.

13. An identification method according to claim 12, wherein said shell material contains or comprises one or more chemical groups which give a measurable SERS response which can be used as the SAISC.

14. An identification method according to claim 13, wherein the SERS particle comprises an additional SAISC.

15. An identification method according to claim 1, wherein said surfactant material comprises the SAISC.

16. An identification method according to claim 1, wherein the concentration of the SERS-active taggant compound in the sample is calculated from the SERS response ratio SATC:SAISC.

17. A product identification system comprising:
   a. A quantity of a SERS-active taggant compound; and
   b. A quantity of SERS particles each SERS particle comprising:
      i. a core comprising a nanoparticle having a plasmonic surface,
      ii. a SERS-active internal standard compound adjacent said plasmonic surface, wherein the SERS-active internal standard compound is not an isotopically-altered version of the SERS-active taggant compound, and
      iii. a shell, said shell encapsulating said core and said SERS-active internal standard compound;
   characterised in that said SERS-active taggant compound and said SERS-active internal standard compound are selected so that said SERS-active internal standard compound has a SERS spectrum containing at least one band which is distinguishable from all of the bands in the SERS spectrum of the SERS-active taggant compound upon excitation by the same or a different excitation wavelength.

18. A product identification system according to claim 17, wherein said shell includes functional portions which are capable of binding to the SERS-active taggant compound.

19. A product identification system according to claim 17, further comprising a Raman spectrometer and a data processor associated therewith for calculation of the concentration of the SERS-active taggant compound from the SERS response of the SERS-active taggant compound and the SERS response of the SERS-active internal standard compound.

20. A method of estimating the concentration of a SERS-active analyte compound in a composition comprising the steps of:
   a) obtaining a sample of said composition;

b) adding to said composition a plurality of SERS particles to form a mixture, each SERS particle comprising:
a core comprising a nanoparticle having a plasmonic surface,
a SERS-active internal standard compound adjacent said plasmonic surface, wherein the SERS-active internal standard compound is not an isotopically-altered version of the SERS-active taggant compound, and
a shell, said shell encapsulating said core and said SERS-active internal standard compound;
c) obtaining a SERS spectrum from said mixture
d) calculating the SERS response ratio SATC:SAISC from the SERS response of the SERS-active analyte compound and the SERS response of the SERS-active internal standard compound.

* * * * *